United States Patent
Weigl

(10) Patent No.: US 6,887,299 B2
(45) Date of Patent: May 3, 2005

(54) AIR IMPROVER AND METHOD FOR AIR IMPROVEMENT IN SPACES

(75) Inventor: Adolf Weigl, Englewood, FL (US)

(73) Assignee: Lidia Weigl, Englewood, FL (US)

( * ) Notice: Subject to any disclaimer, the term of this patent is extended or adjusted under 35 U.S.C. 154(b) by 0 days.

(21) Appl. No.: 10/173,140

(22) Filed: Jun. 17, 2002

(65) Prior Publication Data

US 2003/0183078 A1 Oct. 2, 2003

(30) Foreign Application Priority Data

Mar. 27, 2002 (DE) .......................................... 102 13 889

(51) Int. Cl.$^7$ ................................................. A61L 9/00
(52) U.S. Cl. ............................... 95/26; 96/222; 96/224; 96/227; 422/122; 422/124; 422/5; 261/26; 261/DIG. 88
(58) Field of Search ................................. 454/157, 328; 261/26, 100, 104, 106, DIG. 88, 107; 422/122, 123, 124, 5, 28, 186.3; 96/222, 223, 224, 227, 424; 95/26

(56) References Cited

U.S. PATENT DOCUMENTS

| | | | | |
|---|---|---|---|---|
| 3,576,593 A | * | 4/1971 | Cicirello | 422/4 |
| 3,796,541 A | | 3/1974 | Gentil | 21/110 |
| 4,303,617 A | * | 12/1981 | Bryson | 422/123 |
| 4,759,501 A | * | 7/1988 | Silvenis et al. | 239/6 |
| 5,015,442 A | * | 5/1991 | Hirai | 422/121 |
| 5,302,359 A | * | 4/1994 | Nowatzki | 422/306 |
| 5,756,047 A | * | 5/1998 | West et al. | 422/37 |
| 5,832,320 A | | 11/1998 | Wittek | 396/106 |
| 5,957,771 A | | 9/1999 | Baek | 454/233 |
| 5,963,302 A | | 10/1999 | Wittek | 352/38 |
| 6,065,301 A | | 5/2000 | Akazawa | 62/303 |
| 6,264,887 B1 | | 7/2001 | Farmer | 422/5 |
| 6,270,720 B1 | | 8/2001 | Mandish | 422/4 |
| 6,379,242 B1 | * | 4/2002 | Wiseman et al. | 454/337 |
| 6,536,746 B2 | * | 3/2003 | Watkins | 261/26 |
| 6,713,024 B1 | * | 3/2004 | Arnell et al. | 422/124 |

FOREIGN PATENT DOCUMENTS

| | | | | |
|---|---|---|---|---|
| DE | G 90 03 654.9 | 3/1990 | | F24F/6/00 |
| DE | 19742 358 A1 | 9/1997 | | F24F/3/16 |
| DE | 199 44 340 C2 | 9/1999 | | A61L/9/12 |
| WO | WO 96/31741 | 10/1996 | | F24F/3/12 |
| WO | WO 97/10475 | 3/1997 | | F24F/3/12 |

* cited by examiner

Primary Examiner—Frank M. Lawrence
(74) Attorney, Agent, or Firm—Bromberg & Sunstein LLP

(57) ABSTRACT

An air improver device and method for air improvement in spaces. The device for air improvement for an air-conditioning system comprises a metering mechanism which carries out a controllable metering of the quantity of an active substance discharged per unit time. The device further includes an absorbent receiving carrier, onto which the active substance discharged by the metering mechanism is metered.

28 Claims, 4 Drawing Sheets

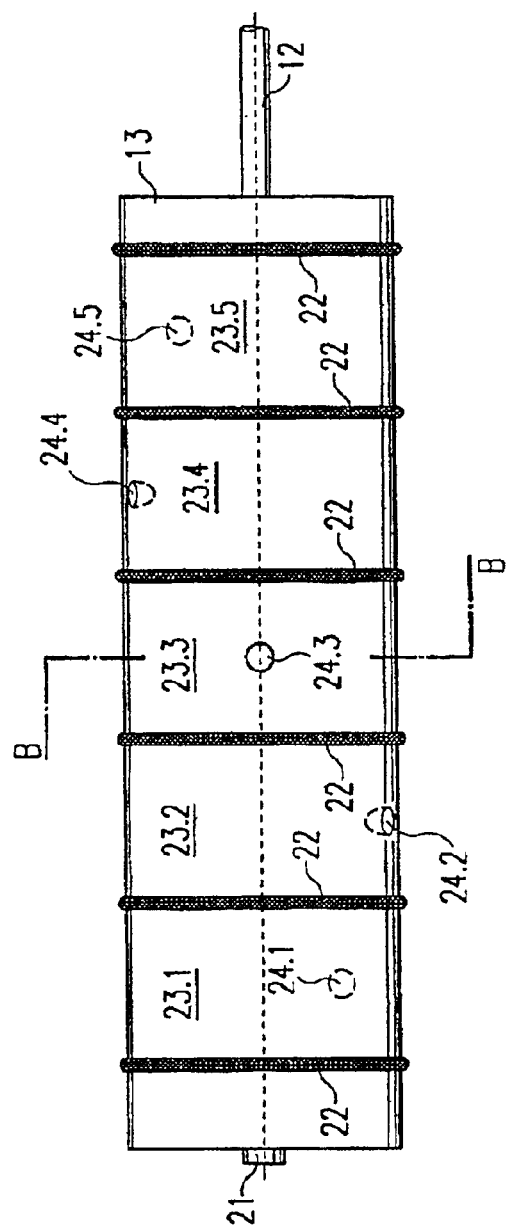
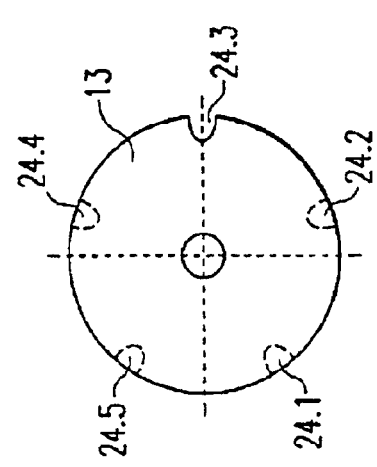
Fig. 4
Fig. 5

AIR IMPROVER AND METHOD FOR AIR IMPROVEMENT IN SPACES

CROSS REFERENCE TO RELATED APPLICATIONS

This application claims priority from German patent application Serial No. 102 13 889.3, entitled "Luftvebesserer und Verfahren zur Luftverbesserung in R äumen" filed on Mar. 27, 2002, which is hereby incorporated by reference, in its entirety.

TECHNICAL FIELD AND BACKGROUND ART

The present invention relates to a device and a method for air improvement in air-conditioned spaces.

In virtually all spaces used by people, unpleasant or disturbing odors may occur which are detrimental to the wellbeing of persons spending time in them. In air-conditioned spaces, such as, for example, supermarkets, banks, hairdressing salons, restaurants and discotheques, but also in a home or the interior of a motor vehicle, disturbing odors are in many cases caused by the characteristic odor of the running air-conditioning system. Further odor emissions may be caused by activities, such as cooking, etc., or, particularly where there are large amounts of people in closed spaces, may be brought about by human perspiration.

There are various known measures for neutralizing or drowning unpleasant odors in spaces. For motor vehicles, what may be referred to as fragrant pinetrees are offered, which, hung behind the rear-view mirror, are intended to improve the odor in the motor vehicle. However, these fragrant pinetrees, which are fleeces impregnated with an aromatic substance, act for only a short time.

A further known product of the type of a mass-produced article is a perfumed felt ring that is placed from above onto the incandescent lamp. When the incandescent lamp is switched on and therefore heat is generated, the felt ring releases scents to an increased extent. This product, too, has a very limited useful life and the disadvantage that the odor emission is initially too strong and later too weak, that is to say the emission cannot be metered.

Furthermore, particularly for use in private houses, electrically operated fragrance dispensers are known, which are plugged into the socket. By means of the current obtained from the socket, heat is produced via a heating winding and causes perfumed liquids, gels or crystals to evaporate. These fragrance dispensers, too, are used up very quickly, and have only a local effect and cannot be controlled centrally.

Moreover, it is already known to couple fragrance dispensers to an air-conditioning system. U.S. Pat. No. 6,264,887 B1 describes a clip, made of a perfumed material, which is inserted into the outlet grid of an air-conditioning system. U.S. Pat. No. 6,270,720 B1 shows an air-conditioning system, in which a channel capable of being filled with an evaporable liquid is accommodated. By the channel being heated, a scent contained in it can be evaporated. One disadvantage is that, even when heating is deactivated, a consumption of scent occurs, at least until all the liquid has evaporated out of the channel.

U.S. Pat. No. 6,065,301 relates to a system for cleaning an evaporator in a motor vehicle air-conditioning system or for feeding odor-active or antibacterial substances into the system. For this purpose, a nozzle bar arranged downstream of the blower in the flow path is provided for atomizing the corresponding liquid. Continuous enrichment of the air-flow with the aromatic or antibacterial active substances is not possible.

U.S. Pat. No. 5,963,302 and U.S. Pat. No. 5,832,320 describe systems, by means of which various fragrances can be added to a ventilation system via a scent wheel similar to a revolver. The metering control takes place via a connectable bypass line. Use in cinemas and the like is intended.

U.S. Pat. No. 5,957,771 relates to an aroma spray mechanism which is integrated into an air-conditioning system and which is implemented by means of a solenoid valve. The spray mechanism allows only a pulsed enrichment of the air flow in the air-conditioning system with scents.

SUMMARY OF THE INVENTION

An object on which the invention is based is to provide a device and a method for air improvement in spaces, which allows a continuous enrichment of an air flow with an active substance. In particular, the device or the method is to be capable of being used in air-conditioning systems for the greatest possible variety of space sizes and is to satisfy practical requirements under the most diverse possible conditions. Furthermore, in particular, good meterability is also to be capable of being achieved.

In accordance with one embodiment of the invention, the device comprises a metering mechanism which carries out a controllable metering of the quantity of an active substance discharged per unit time. Furthermore, the device has an absorbent receiving carrier which is provided in a duct of the air-conditioning system and onto which the active substance discharged by the metering mechanism is metered.

The absorbent receiving carrier has the effect that the active substance discharged by the metering mechanism is not added to the air flow in the air-conditioning system abruptly, but over a defined period of time. A desired degree of impregnation of the receiving carrier can be set and maintained by the metering mechanism. Continuous enrichment of the airflow with the active substance can thereby be achieved. Nevertheless, by virtue of the metering mechanism, the device has a good variability, controllable over a wide range, in the admixing of the active substance, so that the most diverse possible conditions (small spaces or large volume buildings, operation of the air-conditioning system in the cooling or the heating mode) can be taken into account.

Preferably, the metering mechanism is connected to a control unit of a an air-conditioning apparatus of the air-conditioning system. In the simplest form, the control involves activating and deactivating the metering mechanism according to the on/off operating state of the air-conditioning apparatus, for example by the control being supplied with the switched operating voltage of the air-conditioning apparatus. What is achieved thereby is that the metering mechanism is in operation and discharges the active substance only when the air-conditioning apparatus is running. On the other hand, by the air-conditioning apparatus being switched off, the metering mechanism is also switched off. This consequently prevents the situation where a consumption of active substance occurs when the air-conditioning apparatus is switched off (for example, in business spaces at the weekend).

Moreover, the metering quantity can also be controlled as a function of the operating state of the airconditioning apparatus. With the air-conditioning apparatus switched on, for example, it is possible to control the metering mechanism as a function of the air throughput in the air-conditioning apparatus (i.e. the fan power in the air-conditioning apparatus) or of other operating parameters, such as, for example, a cooling or heating of the air in the air-conditioning apparatus. An exact coordination of the metering mechansim with the air-conditioning apparatus used can thus be achieved for virtually all situations and conditions.

The metering mechanism is preferably an electromechanical metering mechansim, even though purely mechanically operating metering mechansims, for example such as are known from medical applications (drop infusions, in which a flexible hose guiding the active substance is compressed in an adjustable way by an asymmetric cam wheel or another squeezing mechanism), are possible. In the case of purely mechanically acting metering mechansims, the metering setting is carried out manually, although, here too, an on/off control can be provided via an electric shutoff valve controlled by the air-conditioning apparatus.

An electromechanical metering mechanism preferably uses an electric motor, in particular a synchronous electric motor, as the electromechanical drive. Metering is in this case influenced by the control of the rotational speed of the electric motor.

According to a particularly preferred refinement of the metering mechanism, the latter comprises a first part, which is connected via a delivery line to an active substance reservoir and which has an orifice for discharging the active substance, a second part, which comprises a transport depression for receiving the active substance discharged from the orifice of the first part, and an electromechanical drive, which brings about a relative movement of the two parts in such a way that the transport depression is guided past the orifice for discharging the active substance and is at the same time filled. The receiving volume of the transport depression in this case defines the smallest quantity of active substance to be metered.

Preferably, the first part is a cylinder, the inner wall of which is provided with the orifice for discharging the active substance, and the second part is a rotary roller, the outer surface of which is provided with the transport depression. Such an electromechanical metering mechanism is mechanically robust and is suitable for long-term use even in large-volume air-conditioning systems.

Since a plurality of transport depressions are provided, distributed over the circumference of the outer surface, the transport capacity of the metering mechanism is increased, for a given rotational speed of the rotary roller, by a reduction in the metering time intervals.

A further advantageous refinement of the invention is defined in that the first part has a plurality of orifices for discharging the active substance and the second part has a plurality of transport depressions for receiving the active substance. By the selective closing of outlet orifices which match with the orifices for discharging the active substance and with the transport depressions, the device can be adapted to the most widely differing possible dimensionings of the air-conditioning system or of the air-conditioning apparatus contained in the latter or can be used for different odor intensities. Furthermore, a plurality of outlet orifices allows a more uniform and larger-area distribution of the active substance via the absorbent receiving carrier, this likewise having a beneficial influence on the capacity and the operating behavior of the device.

Preferably, the absorbent receiving carrier consists of a fiber-containing and/or open-pored material, in particular cellulose or an absorbent paper. These materials, on the one hand, make it possible to have a good lateral distribution of the active substance in the receiving carrier and consequently provide an evaporation area of sufficient size and, on the other hand, exhibit a storage behavior for the active substance which has the effect that, even in a metering of active substance which has discrete values in time, a discharge, essentially uniform over time, of active substance to the air flow is achieved.

Preferably, the device comprises holding means for the receiving carrier, said holding means being firmly connected in structural terms to the metering mechanism. The device in this case forms a structural unit which can be mounted in a simple way in the duct provided for it in the air-conditioning system.

Preferably, the holding means is an interchangeable holder, in particular in the form of a push-in frame, for the receiving carrier. This measure allows a simple exchange of receiving carriers which are soiled or are to be renewed for other reasons.

The active substance is preferably a scent essence and/or an antibacterially acting essence. However, active substances with other actions may also be administered.

Preferably, the device is installed in a duct of an air-conditioning system for the air-conditioning of a space or building. However, the use of the device in an air-conditioning system of a motor vehicle is also possible and provided.

BRIEF DESCRIPTION OF THE DRAWINGS

The foregoing features of the invention will be more readily understood by reference to the following detailed description, taken with reference to the accompanying drawings, in which:

FIG. 4 shows a side view of a rotary roller with transport depressions of the device;

FIG. 5 shows a cross section along the line B—B in FIG. 4; and

DETAILED DESCRIPTION OF SPECIFIC EMBODIMENTS

Figure 1:
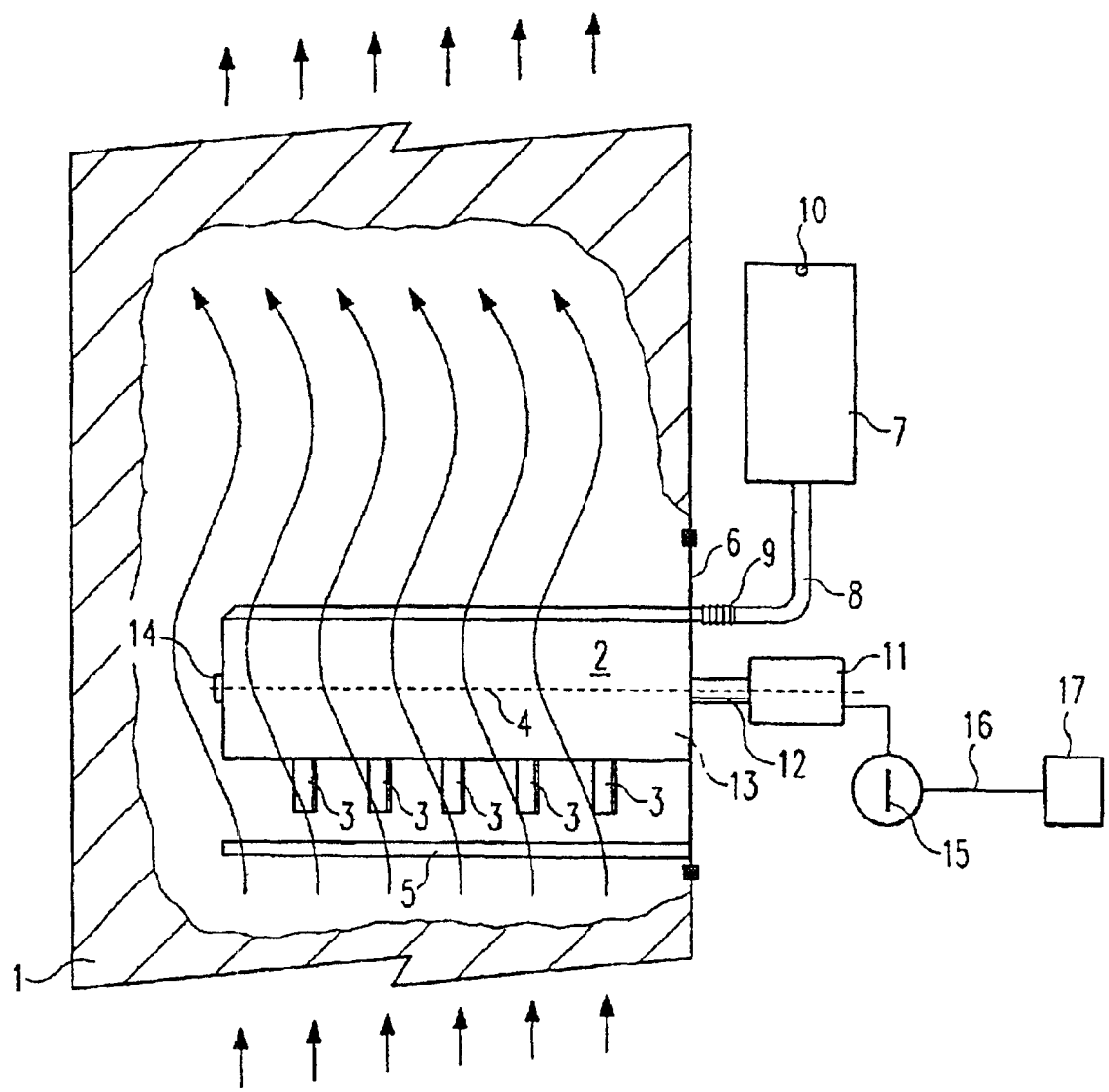
FIG. 1 shows, in a side view, a partially cut away illustration of the device installed in a duct.

FIG. 1 shows, in a diagrammatic illustration, an exemplary embodiment of an air enrichment device according to the invention in the installed state. A duct 1 of an air-conditioning system extends in the vertical direction in FIG. 1 and is illustrated, partially cut away. The air flow upstream of, through and downstream of the duct portion shown is indicated by arrows.

Air-conditioning systems for buildings or houses are designed as circulation systems for energy saving reasons. Air is extracted from a space or a plurality of spaces either near the floor or through shafts in the ceiling region and is delivered via a duct system for a central air-conditioning apparatus (not illustrated). The air-conditioning apparatus comprises a cold-air assembly (evaporator), usually also a heating system and one or more impellers for transporting the air flowing through the air-conditioning apparatus. The air flow discharged by the air-conditioning apparatus passes first into a central duct which is divided along the further flow path into a duct system consisting of a plurality of individual ducts. Depending on the structural conditions of the house or building to be air-conditioned, the duct system is designed and executed in such a way that effective air-conditioning is achieved in the entire space or building.

The duct portion 1 illustrated in FIG. 1 is located preferably in the central duct on the outflow side of the air-conditioning apparatus. In this case, air improvement is achieved in all the spaces supplied by the air-conditioning apparatus. In principle, however, the portion 1 may also be a duct arranged on the inflow side with respect to the air-conditioning apparatus, a duct within the air-conditioning apparatus or an individual duct of the duct system described. Furthermore, there is, of course, also the possibility of providing only a single ventilation duct, that is to say of dispensing with the branched duct system.

The duct 1 may be a commercially available duct for an air-conditioning apparatus, for example for a home. Such a duct is, for example, 50 cm wide and 40 cm deep and consists of galvanized sheet metal.

The air enrichment device has a cylinder 2, illustrated in a side view, which comprises, distributed over the length, 5 outlet orifices 3 on its lower region. The cylinder axis is illustrated by the broken line 4. Opposite the outlet orifices 3 is arranged a receiving carrier 5. The receiving carrier 5 consists of an absorbent material, for example, a fleece consisting, in particular, of neutral cellulose or absorbent paper. As is clear in FIG. 1, the receiving carrier 5 is located in the air flow, so that an active substance metered through the outlet orifices 3 is evaporated and transported away in the air flow.

The cylinder 2 and the receiving carrier 5 can be structurally connected to one another in a way illustrated in more detail later and be mounted, for example, on a removable element 6 of the duct wall.

Located outside the duct 1 is an active substance container 7 which is liquid-connected via a delivery line 8 to a connection 9 or an integrated duct of the cylinder 2. The active substance container 7 is equipped in its upper region with a ventilation valve 10 which prevents the occurrence of a vacuum when the active substance container 7 is emptied.

Figure 2:
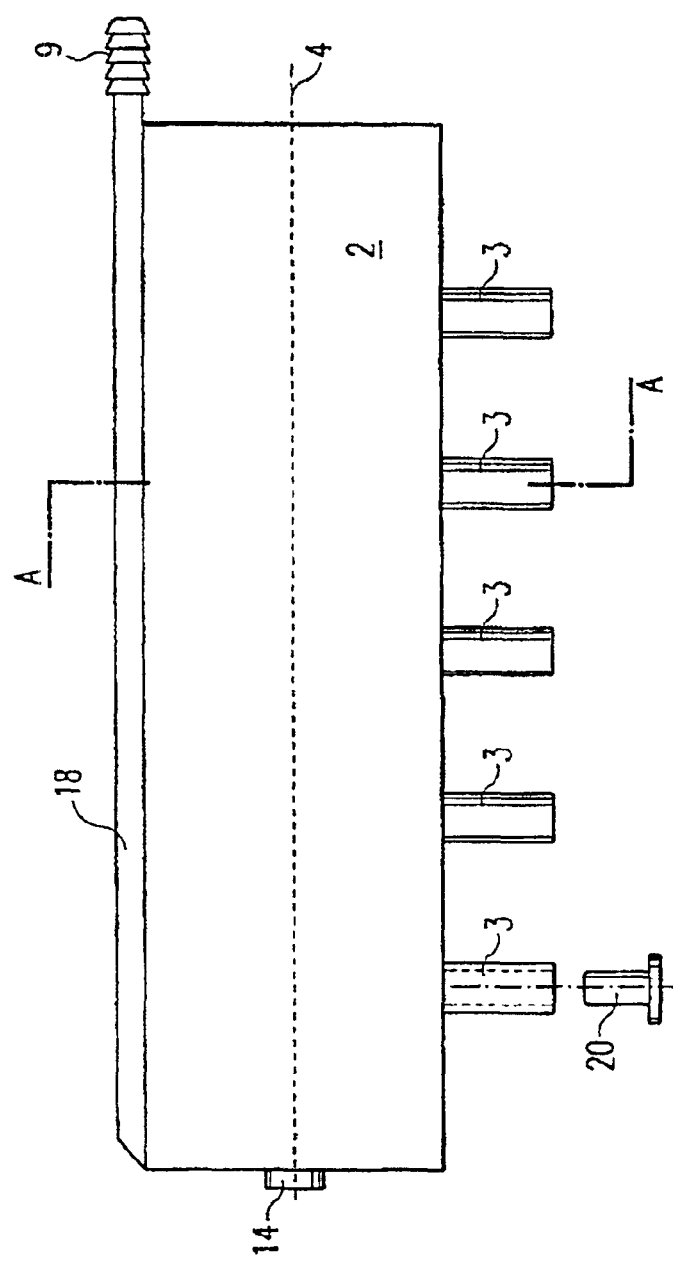
FIG. 2 shows a side view of the cylinder of the device shown in FIG. 1.

A synchronous motor 11 drives the shaft 12 of a rotary roller 13, which cannot be seen in FIG. 1, which is located within the cylinder 2 and is rotatably mounted in a cylinder 2 by means of an axial receptacle 14 of the latter, see also FIG. 2.

The synchronous motor 11 is preceded by a rotational speed controller 15, by means of which the rotational speed of the synchronous motor 11 can be set with high accuracy. The rotational-speed controller 15 obtains its operating voltage, via an electrical delivery line 16, from the air-conditioning apparatus 17 illustrated merely diagrammatically in FIG. 1. What is achieved thereby is that, when the air-conditioning apparatus 17 is switched off, the synchronous motor 11 is also switched off automatically. Moreover, in a way not illustrated, between a control unit of the air-conditioning apparatus 17 and the rotational-speed controller 15, further electrical control lines can be provided, via which it becomes possible, by means of the air-conditioning apparatus 17, to have a control functionality of the rotational-speed controller 15 which goes beyond switch-on and switch-off. In the case of a reduced operation of the air-conditioning apparatus 17, with reduced fan power and therefore a reduced air throughput, the rotational speed of the synchronous motor 11 can also be reduced in proportion to this. Furthermore, the control of the motor rotational speed can take place as a function of the temperature setting of the air-conditioning apparatus 17. Control connections of this type may be implemented, for example, via data lines which are to be connected to a programmable interface of the air-conditioning apparatus 17.

Figure 3:
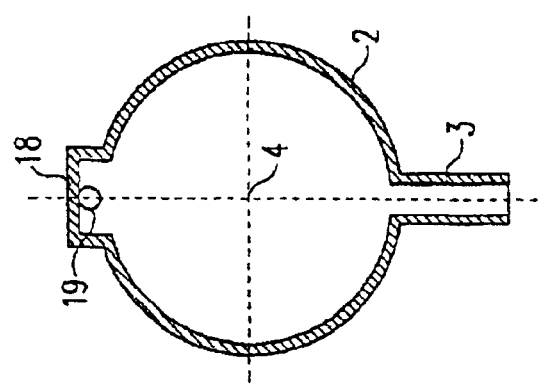
FIG. 3 shows a cross section through the cylinder along the line A—A in FIG. 2.

FIG. 2 shows the cylinder 2 in an enlarged illustration. A cross section along the line A—A through the cylinder 2 is illustrated in FIG. 3. In its upper region, the wall of the cylinder 2 is designed in the form of a duct 18. Located in the wall duct 18 running parallel to the cylinder axis 4 is an inflow tube 19 which is connected to the connection 9.

The outlet orifices 3 can be closed sealingly by means of plugs or closing caps 20.

FIGS. 4 and 5 show the rotary roller 13 respectively in a side view and in cross section along the line B—B. The outside diameter of the rotary roller 13 corresponds, with the exception of minimal movement clearance, to the inside diameter of the cylinder 2. In the installed state, a journal 21 arranged centrally on the free end wall is mounted in the axial receptacle 14 of the cylinder 2. The shaft 12 extends on the opposite side of the rotary roller 13.

In the example illustrated here, the rotary roller 13 is subdivided, by means of 6 sealing rings 22 arranged, distributed at equal intervals over the roller length, into five portions 23.1, 23.2, 23.3, 23.4 and 23.5 sealed off relative to one another. The axial sealing rings 22, consisting of an acid- and oil-resistant material, for example neoprene, prevent an exchange of liquid between said portions 23.1 to 23.5. A transport depression 24.1, 24.2, 24.3, 24.4 and 24.5 is formed in each portion 23.1, 23.2, 23.3, 23.4, and 23.5. FIG. 5 shows that the transport depressions 24.1 to 24.5 are arranged, distributed equidistantly in the circumferential direction over the surface of the rotary roller 13. The radial angle between adjacent transport depressions is 72° in the example, shown here, with 5 transport depressions. The transport depressions 24.1 to 24.5 match in their axial position with the outlet orifices 3 of the cylinder 2.

The device operates as follows. Where transport depression 24.1 to 24.5 comes into the region of the wall duct 18 as a result of the rotation of the rotary roller 13, said transport depression is loaded with the active substance, normally a liquid. The quantity of active substance to be transported is determined by the receiving volume of the transport depression 24.1 to 24.5 and may amount, for example to about 1 to 2 g when oil is used as the active substance liquid. During further rotation of the rotary roller 13, the transport depression 24.1, 24.2, 24.3, 24.4 or 24.5 filled with the active substance is led along the inner wall of the cylinder 2 as far as the matching outlet orifice 3. The virtually identical outside and inside diameters of the rotary roller 13 and of the cylinder ensure that the active substance is delivered to the outlet orifice 3 in a controlled manner and without any loss. As soon as the transport depression 24.1 to 24.5 comes into the region of the outlet orifice 3, the transport depression 24.1 to 24.5 is emptied and (insofar as the outlet orifice 3 is not closed) the active substance comes onto the receiving carrier 5.

As a rule, the active substance liquid has the effect 5 of lubricating the system. In order to prevent the rotary roller 13 from running dry in the cylinder 2 when the active substance container 7 is empty, a safety switch (not illustrated) may be provided, which is triggered when the active substance container 7 is empty and causes the supply of current via the electrical delivery line 16 to the synchronous motor 11 to be interrupted.

The safety switch used may be, for example, a mercury switch or a noncontacted proximity switch which is accommodated in a specific measurement housing (not illustrated) integrated into the active substance delivery line 8. As soon as the liquid level in the measurement housing falls, this is recorded by a float (in the case of the proximity switch, for example, a magnet embedded in acid-resistant PU foam) and the switch is triggered below a defined liquid level or when the measurement housing is empty. The switch may in this case also activate a visual warning indicator.

A scented oil is considered below as an active substance liquid without any restriction in generality. A receiving carrier 5 consisting of cellulose swells somewhat by being wetted with scented oil. The absorbency of the cellulose carrier causes both a distribution of the scented oil over the receiving carrier 5 and some storage of the scented oil within the receiving carrier 5. The latter aspect has the effect that the characteristic odor of the oil is not discharged into the surroundings in the duct 1 abruptly, but over a lengthy period of time.

The result of tests in approximately 300 m² large and 3.3 m high fully air-conditioned home was that, when a felt carrier with the size 80×30×2 mm was used, the felt carrier wetted with some drops of a commercially obtainable scented oil instantaneously spread a sweet-smelling scent throughout the entire home after the air-conditioning apparatus was switched on. Without the felt carrier being rewetted, this state persisted for about 6 to 7 hours, with the air-conditioning apparatus being on average power. Thereafter, the intensity of the scent decreased slowly. As soon as two to three drops of the oil were applied to the felt carrier every 5 to 6 hours, a constantly uniform scent prevailed in all the spaces of the home, without the metering intervals becoming noticeable. A corresponding design is provided for the device according to the invention.

The device according to the invention has a multiplicity of possibilities of variation for controlling the odor intensity and for adapting the apparatus to different practical situations and building or space sizes.

A first possibility of variation arises as a result of the closability of the outlet orifices 3. If, for example, the synchronous motor 11 executes one revolution in 24 hours, one to five drops of scented oil, depending on the number of opened outlet orifices 3, can be applied to the receiving carrier 5 within 24 hours.

A second possibility for continuous regulation involves increasing the motor rotational speed.

In structural terms, there may be provision, according to a third possibility of variation, for providing in each portion 23.1 to 23.5 of a plurality of transport depressions 24.1 to 24.5 arranged, distributed on the circumference. In this case, the capacity of the system increases.

Furthermore, there is the possibility of providing, instead of the five portions 23.1 to 23.5, each with one transport depression, an individual portion (in the form of a transport wheel) with, for example, five transport depressions arranged, distributed on the circumference.

In a further variant, the receiving volume of transport depressions 24.1, 24.2, 24.3, 24.4 and 24.5 located in various portions 23.1 to 23.5 is configured differently. By means of this measure, the working range of the device can be increased considerably by the selective closing or opening of suitable outlet orifices 3.

Finally, there is the possibility of providing a plurality of inflow tubes 19 and thereby allowing the simultaneous addition of a plurality of different active substances to the air flow. For example, in addition to a scent, a antibacterial active substance contained in a separate container (not illustrated) may also be used. In this case, some of the portions 23.1 25 to 23.5 are provided for metering the scent and the remaining portions 23.1 to 23.5 for metering the antibacterial active substance. The antibacterial active substance may also be used instead of the scent.

Moreover, an (odor-neutral) antibacterial action can be achieved by using a UV lamp installed in the duct 1. High efficiency can be achieved by intensive illumination of the duct. The UV lamp is switched in such a way that it lights up only when the air-conditioning apparatus or the air enrichment device according to the invention is in operation. In particular, the UV lamp may be mounted directly on the air enrichment or metering device according to the invention.

Figure 6:
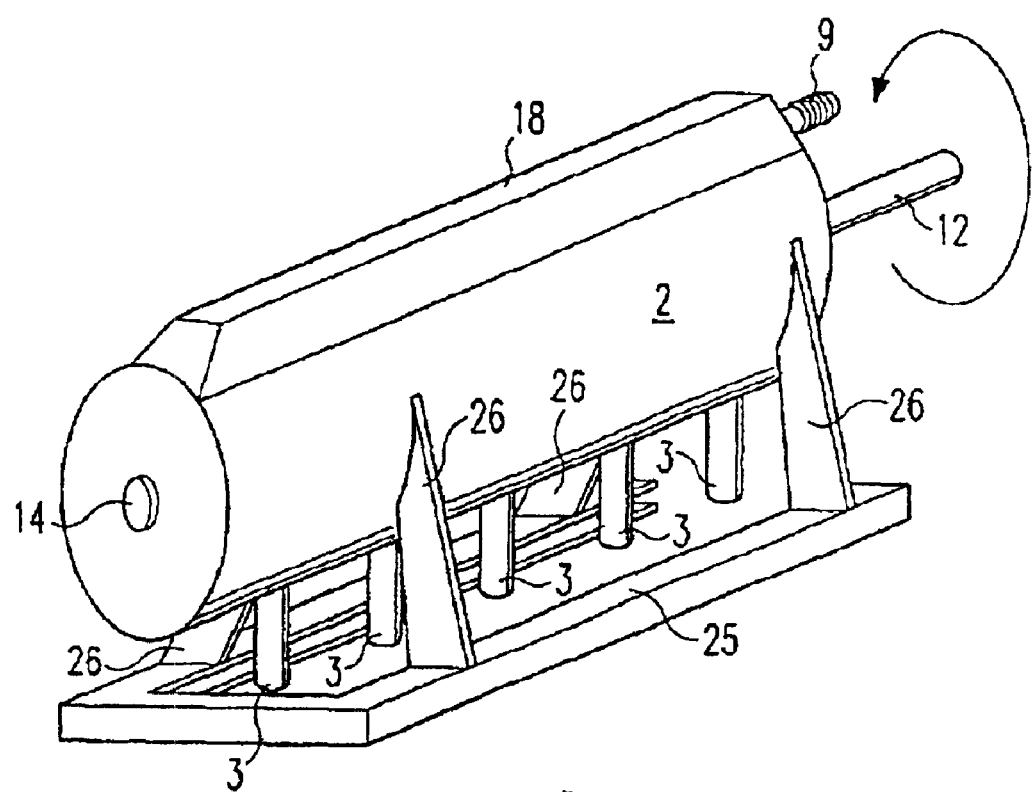
FIG. 6 shows a perspective illustration of a device according to the exemplary embodiment of the invention.

FIG. 6 shows the exemplary embodiment in a perspective illustration. A frame 25 designed as a U-profile is firmly connected to the cylinder 2 via struts 26. The receiving carrier 5 is pushed into the open region of the frame 25 and, after the device has been mounted, is secured by the wall element 6 of the duct 1. When the receiving carrier 5 is exchanged, the latter is drawn out of the frame 25 after the opening of the duct 1 and is replaced by a new receiving carrier 5. Quick-action fastenings acting by means of clips or other holding elements may likewise be envisaged.

In conclusion, it may be stated that the device according to the invention, by virtue of its high variability, is suitable for the most diverse possible fields of use and provides continuous and exactly adjustable admixing of an active substance over a wide quantity range, along with the uniform odor intensity.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A device for air improvement for an air-conditioning system, comprising:
    an electromechanical metering mechanism for controlling the enrichment of the air flow with scent essence, the electromechanical metering mechanism including a metering void of predefined volume and being adapted to intermittently meter a defined quantity of the scent essence per adjustable metering time interval by filling the predefined volume with scent essence without discharging scent essence, and by subsequently discharging the scent essence out of the predefined volume without filling the same each adjustable metering time interval; and
    an absorbent receiving carrier which is provided in a duct of the air-conditioning system and onto which the scent essence discharged by the metering mechanism is metered.

2. The device according to claim 1, wherein the metering mechanism is connected to a control unit of an air-conditioning apparatus of the air-conditioning system.

3. The device according to claim 1, wherein the air-conditioning system is an apparatus for the air-conditioning of a building, and wherein the duct is a central duct of the air-conditioning system.

4. The device according to claim 1, wherein the electromechanical metering mechanism uses an electric motor, in particular a synchronous electric motor, as an electromechanical drive.

5. The device according to claim 4, wherein the device comprises a unit for controlling the rotational speed of the electric motor.

6. A device for air improvement for an air-conditioning system, comprising:
- an electromechanical metering mechanism that controllably meters a quantity of an active substance discharged per unit time, the mechanism including:
  - a first part, which is connected via a delivery line to an active substance reservoir and which has an orifice for discharging the active substance;
  - a second part, which comprises a transport depression for receiving the active substance discharged from the orifice of the first part, and
  - an electromechanical drive which brings about a relative movement of the two parts in such a way that the transport depression is guided past the orifice for discharging the active substance and is at the same time filled; and
- an absorbent receiving carrier which is provided in a duct of the air-conditioning system and onto which the active substance discharged by the metering mechanism is metered.

7. The device according to claim 6, wherein the first part is arranged so as to be fixed in position in relation to the duct, and the second part is acted upon by the electromechanical drive.

8. The device according to claim 6, wherein the first part is a cylinder, the inner wall of which is provided with the orifice for discharging the active substance, and the second part is a rotary roller, the outer surface of which is provided with the transport depression.

9. The device according to claim 8, wherein a plurality of transport depressions are provided, distributed over the circumference of the outer surface.

10. The device according to claim 6, wherein the first part has a plurality of orifices for discharging the active substance and the second part has a plurality of transport depressions for receiving the active substance.

11. The device according to claim 1, wherein the electromechanical metering mechanism has a plurality of outlet orifices for discharging the active substance.

12. The device according to claim 11, wherein the outlet orifices can be closed selectively by a means of closures.

13. The device according to claim 1, wherein the absorbent receiving carrier consists of a fiber-containing and/or open-pored material, in particular cellulose or an absorbent paper.

14. The device according to claim 1, wherein the device comprises a holding means for the receiving carrier, said holding means being firmly connected in structural terms to the metering mechanism.

15. The device according to claim 14, wherein the holding means is designed as an interchangeable holder, in particular in the form of a push-in frame, for the receiving carrier.

16. The device according to claim 1, wherein the air-conditioning system is an apparatus with a plurality of ventilation ducts for the air-conditioning of a building having a plurality of ventilated spaces, and the duct is a central duct of the air-conditioning system, from which the plurality of ventilation ducts branch off downstream of the air improvement device in the direction of flow.

17. The device according to claim 1, wherein the metering mechanism is provided for installation in the duct of the air-conditioning system.

18. The device according to claim 1, wherein the metering mechanism is coupled to a UV lamp.

19. A method for air improvement for an air-conditioning system of a building, comprising:
- intermittent metering of a defined quantity of a scent essence per adjustable metering time interval onto an absorbent receiving carrier in a central duct of an air-conditioning system by an electromechanical metering mechanism for controlling the enrichment of the air flow with scent essence by filling a metering void of predefined volume with scent essence without discharging scent essence, and by subsequently discharging the scent essence out of the predefined volume without filling the same on the absorbent receiving carrier each adjustable metering time interval.

20. The method according to claim 19, further comprising:
- controlling the metering quantity of active substance discharged by the metering mechanism as a function of the operating state of an air-conditioning apparatus of the air-conditioning system.

21. The method according to claim 19, wherein the metering mechanism is an electro-mechanical metering mechanism, and wherein controlling the metering quantity includes setting the rotation speed of an electric motor, in particular a synchronous electric motor, which forms the drive of the electromechanical metering mechanism.

22. A method for air improvement, comprising:
- metering of an active substance onto an absorbent receiving carrier in a duct of an air-conditioning system by a controllable electromechanical metering mechanism;
- controlling the metering quantity of active substance discharged by the metering mechanism as a function of the operating state of an air-conditioning apparatus of the air-conditioning system, the controlling of the metering quantity including:
  - setting the rotation speed of an electric motor, in particular a synchronous electric motor, which forms the drive of the electromechanical metering mechanism;
  - filling of a transport depression present in a movable part with the active substance;
  - moving of the filled transport depression in relation to an outlet orifice of the metering mechanism by the movement of the part by an electromechanical drive; and
  - discharging the active substance from the transport depression through the outlet orifice of the metering mechanism.

23. A device for air improvement for an air-conditioning system, comprising:
- a metering means for intermittent metering of a defined quantity of scent essence discharged per adjustable metering time, wherein the metering means fills a metering void of predefined volume with scent essence without discharging scent essence, and subsequently discharges the scent essence out of the predefined volume without filling the same each adjustable metering time interval, and
- an absorbent receiving carrier which is provided in a duct of the air-conditioning system and onto which the active substance discharged by the metering means is metered.

24. The device according to claim 23, wherein the metering means is an electromechanical metering means.

25. The device according to claim 24, wherein the electromechanical metering means uses an electric motor, in particular a synchronous electric motor, as an electromechanical drive.

26. A method for air improvement, comprising:

intermittently metering a defined quantity of scent essence per adjustable metering time onto an absorbent receiving carrier in a duct of an air-conditioning system by a controllable metering means, wherein intermittently metering the defined quantity of scent essence includes filling a metering void of predefined volume with scent essence without discharging scent essence, and subsequently discharging the scent essence out of the predefined volume without filling the same each adjustable metering time interval.

27. The method according to claim 26, further comprising:

controlling the metering quantity of scent essence discharged by the metering means as a function of the operating state of an air-conditioning apparatus of the air-conditioning system.

28. The method according to claim 26, wherein the metering means is an electro-mechanical metering means, and wherein controlling the metering quantity includes setting the rotation speed of an electric motor, in particular a synchronous electric motor, which forms the drive of the electromechanical metering means.

* * * * *